US00PP07958P

United States Patent [19]

Drewlow

[11] Patent Number: Plant 7,958

[45] Date of Patent: Sep. 1, 1992

[54] STREPTOCARPUS PLANT NAMED THALIA

[75] Inventor: Lyndon W. Drewlow, Ashtabula, Ohio

[73] Assignee: Mikkelsens, Inc., Ashtabula, Ohio

[21] Appl. No.: 635,708

[22] Filed: Dec. 28, 1990

[51] Int. Cl.[5] ..... A01H 5/00
[52] U.S. Cl. ..... Plt./87.13
[58] Field of Search ..... Plt./68

*Primary Examiner*—James R. Feyrer
*Attorney, Agent, or Firm*—Foley & Lardner

[57] ABSTRACT

A Streptocarpus plant named Thalia characterized by the combined characteristics of ruffled flowers which are relatively large and white in color with magenta streaking on the lower three petals, numerous short and narrow leaves in rosette form, petal lobes touch approximately half way up the cut, flowers are long lasting and non-shattering, floriferous habit and an ability to continuously flower under low light conditions of winter and high temperatures of summer.

1 Drawing Sheet

The present invention relates to a new and distinct cultivar of streptocarpus plant, botanically known as *Streptocarpus×hybridus,* and known by the cultivar name Thalia. Thalia was developed by me through controlled breeding by crossing Mikkelsen Seedling 85-1272-3 seed parent) with Mikkelsen Seedling 85-1230-4 (pollen parent).

Asexual reproduction by me by leaf cuttings has shown that the unique features of this new Streptocarpus are stabilized and are reproduced true to type in successive propagations.

The following characteristics in combination distinguish this new Streptocarpus from its parent cultivars and from other cultivated streptocarpus of this type known and used in the floriculture industry. The characteristics are expressed by reference to comparison cultivars Ariadne, disclosed in my U.S. Plant Pat. No. 6,396, and Venus, a cultivar which is not patented.

1. Thalia has ruffled white flowers with magenta streaking on the lower three petals from a white throat, while Ariadne has a flat white flower with magenta streaks on the lower three petals from a yellow throat; Venus has a ruffled lavender flower with heavy magenta streaking on the lower three leaves and two yellow streaks in the throat.

2. Thalia has a larger flower (6.0 to 6.5 cm. in diameter) than Ariadne which averages 5.5 to 6.0 cm; and Venus which averages 5.0 to 5.5 cm.

3. The edges of the five petal lobes on Thalia touch the edges of adjacent lobes approximately one half the way up the cut, while Ariadne has a 4 to 6 mm. gap between lobes; and Venus has a 3 to 5 mm. overlap at that point.

4. Thalia and Venus are similar in height at 12 to 13 cm., with Ariadne being 15 to 18 cm; when all are grown under similar conditions. Thalia has a spread of 25 to 30 cm. at maturity, while Venus and Ariadne are 35 to 40 cm. wide at maturity.

5. Thalia has shorter and narrower leaves at 15 to 18 cm. long and 4 to 5 cm. wide, with Venus and Ariadne having leaves that are 20 to 25 cm. long and 8 to 10 cm. wide.

6. Thalia has a green ovary when receptive, while Venus has a green ovary with light purplish cast and Ariadne has a purplish ovary.

7. Thalia and Ariadne have pure white stigmas, while Venus has a slight purplish cast to the white stigma when receptive.

8. Thalia and Venus each average two flowers per bloom stalk, whereas Ariadne averages six.

9. Thalia and Venus have a crenated flower petal margin while Ariadne has an entire margin.

10. Flower bloom stalks of Ariadne and Thalia are green while Venus has a reddish purple cast.

11. Pedicels of first flower to open in the inflorescences of Thalia and Venus are 3 to 4 mm. long, as compared to the pedicels of Ariadne which are 6 to 8 mm. long on the first flower.

The accompanying colored photograph illustrates in top perspective view the overall appearance of Thalia, and showing colors as true as it is reasonably possible to obtain in a colored reproduction of this type. The photograph was taken on Aug. 9, 1990 under natural light on an overcast day under double poly greenhouse covering at Ashtabula, Ohio.

The following is a detailed description of my new streptocarpus cultivar, based on plants produced in greenhouses in Ashtabula, Ohio, during the summer season of the year. Plants were grown in 15 cm. pots and measurements were taken 18 weeks after rooted cuttings were planted. Height measurements were taken from the soil line of the container. The plants were grown at 64°-68° F. night temperatures under 2000-2500 foot candles of light, and with 240 ppm Nitrogen, 240 ppm Potassium, and 175 ppm Phosphorous nutritional levels with trace elements added. Habit of growth, foliage coloration, leaf variegation, size of leaves and flower size will be greatly influenced by nutritional and environmental conditions.

Color references are made to the Royal Horticultural Society Colour Chart except where general terms of ordinary dictionary significance are used.

Parentage: Controlled cross between female Mikkelsen Seedling No. 85-1272-3 and male Mikkelsen Seedling No. 85-1230-4.

Propagation:

(A) *Type cutting.*—Leaf.

(B) *Time to develop plantlets.*—8 weeks at 20° C. summer, 10 weeks at 20° C. winter.

(C) *Rooting habit.*—Fibrous, fine, abundant.

Plant description: (Habit of growth, foliage coloration and size of leaf will be greatly influenced by nutritional and environmental conditions, thus data that follows was taken from plants grown under the conditions stated above.)

(A) *Habit and form of growth.*—Vigorous; leaves are in a rosette extending from a crown at soil line. Leaves form around plant to produce a symmetrical plant with flower stalks forming at basal area of midrib of each mature leaf; flowers are carried above foliage.

(B) *Height from soil line.*—12–13 cm.

(C) *Spread.*—25 to 30 cm. at maturity. (1) Size: 15 to 18 cm. in length and 4.0 to 5.0 cm. wide at widest point. (2) Quantity: More than 15 leaves at maturity. (3) Shape: Elliptical. (4) Texture: Lower surface rugose with veins protruding and pubescent; upper surface rugose and pubescent. (5) Margin: Finely crenate. (6) Color: Young foliage: Top side, 146B; under side 147C. Mature foliage: Top side, 146; under side 147C. (7) Ribs and veins: Pinnate. (8) Rib and vein color: 146D. (9) Leaf tips: Obtuse. (10) Leaf base: Acute.

Flowering description:

(A) *Opening.*—Flowers open one at a time on individual flower stalks.

(B) *Fully expanded.*—55 to 60 mm.

(C) *Stem.*—Single, green in color, round, variable in length, pubescent; several individual stems from a leaf midrib.

(D) *Form.*—Funnel shaped, corolla cylindrical, 5 lobed; lobes orbicular to obovate with two upper petals slightly smaller than the three bottom petals. Open flower has a ruffled appearance. Calyx deeply five parted with no tube.

(E) *Flower buds.*—Immature bud hangs downward, raising as it matures; at maturity bud is 25 to 28 mm. long with five green sepals in the calyx folded over the basal end.

(F) *Flowers borne.*—In clusters of two to four flowers per flower stalk, with two the most common on a mature plant, carried above the foliage; pedicels of upper flowers on stalk are 3 to 4 mm. long and are 7 to 8 mm. long on lower flowers in the inflorescence.

(G) *Quantity of flowers.*—Mature plant can have 20 or more flower stalks open, with up to 4 flowers per stalk.

(H) *Permanence.*—Ten days or longer.

(I) *Flower diameter.*—6.0 to 6.5 cm.

Color:

(A) *Tonality from a distance.*—White with magenta streaking from the throat into the lower three petals with a white throat.

(B) *Front of petals.*—155D with 74B-C streaking from throat into the lower three petals.

(C) *Reverse of petals.*—155D.

(D) *Throat.*—155D and 74B streaking.

(E) *Discoloration.*—Magenta streaking fades to lighter color as flower ages.

Petals:

(A) *Texture.*—Satin.

(B) *Appearance.*—Individual lobes with somewhat crenate margins; top two petals are reflexed and smaller than the bottom petals which are flat and slightly contorted.

(C) *Arrangement.*—Circular in shape with deep cuts between the petals.

(D) *Persistence.*—Petals remain on plant in dry form until picked from plant.

(E) *Fragrance.*—None.

Reproductive organs:

(A) *Stamens.*—Two fertile and two sterile; very small. 1. Anther shape: Two fertile interconnected and flat; color white. 2. Filament: Two fertile and free standing for 7 mm. and sterile for 1 mm. white in color. 3. Pollen color: White.

(B) *Pistels.*—1. Stigma shape: Flattened with reflex tips; color white; 3 mm. in size. 2. Style color: White; 6 mm. in size. 3. Ovaries: Numerous, 12–14 mm. in size, on a receptive pistel; color green.

Disease resistance: No disease problems to date.

OTHER IMPORTANT CHARACTERISTICS THAT HELP DEFINE THE NEW CULTIVAR

1. Thalia has numerous short leaves in a rosette instead of one large leaf that characterized many older streptocarpus cultivars. This results in a cluster of flowers in the middle of green foliage, thereby making an attractive 10 cm. to 15 cm. plant.

2. Flowers are long lasting, non-shattering and leaves are small and pliable, thereby making this cultivar easy to ship.

3. Thalia has shown the ability to flower both under the lower light conditions of winter (December to February) and higher temperatures of summer (July to September), without ever going out of bloom under greenhouse conditions.

4. Thalia has shown the ability to tolerate watering with 40° F. water without foliar spotting and to tolerate fairly high light levels (2500 foot candles) in summer without leaf bronzing.

I claim:

1. A new and distinct cultivar of Streptocarpus plant named Thalia, as illustrated and described.

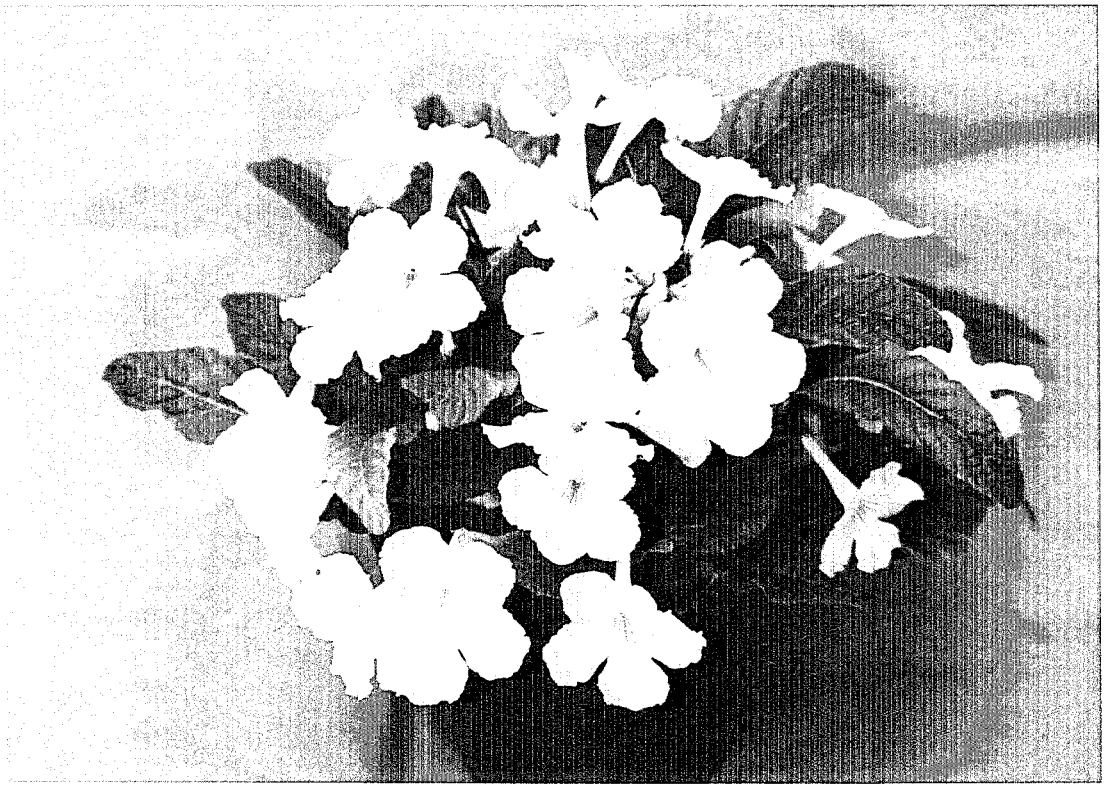

* * * * *